United States Patent [19]

Chapman, deceased

[11] Patent Number: 4,824,922
[45] Date of Patent: Apr. 25, 1989

[54] ACRYLIC SILICATE COMPOSITIONS AND METHODS AND HIGHLY OXYGEN-PERMEABLE POLYACRYLATES MADE THEREFROM

[75] Inventor: Dwain R. Chapman, deceased, late of Adrian, Mich., by Twila V. Chapman, legal representative

[73] Assignee: Fused Kontacts of Chicago, Chicago, Ill.

[21] Appl. No.: 115,179

[22] Filed: Oct. 30, 1987

Related U.S. Application Data

[62] Division of Ser. No. 754,590, Jul. 15, 1985, Pat. No. 4,709,066.

[51] Int. Cl.$^4$ .............................................. C08F 30/08
[52] U.S. Cl. ................................ 526/279; 556/437; 351/160 R
[58] Field of Search ..................... 526/279; 556/437; 351/160 R

*Primary Examiner*—C. Warren Ivy
*Assistant Examiner*—Alex H. Walker
*Attorney, Agent, or Firm*—Lockwood, Alex, FitzGibbon & Cummings

[57] ABSTRACT

A polymer derived from a new composition of matter comprising an acrylic silicate of the type having the general formula:

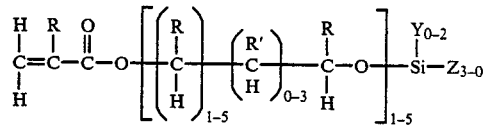

wherein
R=alkyl, aryl or H,
R'=R or OR
Y=alkyl, vinyl, aryl, or fluoroalkyl

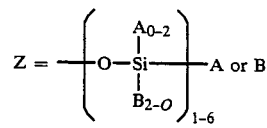

A=Y or H; and
B=Oxyalkyl, oxyaryl, oxyfluoroalkyl, oxyalkylacrylate, alkyl esters, aryl esters, fluoroalkyl esters, or acrylic esters.

This composition may be reacted with polymerizable acrylic esters to form optically transparent, machineable polymers useful in various applications, including use as gas-permeable hard corneal contact lenses.

4 Claims, No Drawings

ACRYLIC SILICATE COMPOSITIONS AND METHODS AND HIGHLY OXYGEN-PERMEABLE POLYACRYLATES MADE THEREFROM

This application is a division, of application Ser. No. 745,590, filed July 15, 1985 now U.S. Pat. No. 4,709,066.

BACKGROUND OF THE INVENTION

The present invention relates generally to silicate compositions, and more particularly, to acrylic and methacrylic silicate materials and copolymers thereof with optically transparent polymerizable materials to form corneal contact lenses. In another aspect, the invention relates to the method of making and using acrylic silicates and to certain co-polymerizable acryloxy alkoxy silicates also useful in such applications.

In recent years, after the general concept of corneal contact lenses became accepted, it become apparent that such contact lenses required improvement in certain areas. Specifically, while some corneal contact lenses afforded great comfort because they were made from soft or relatively flexible materials, such as hydoxyethylmethacrylate ("HEMA") and derivative materials able to absorb water of hydration, or from elastomeric silicone materials, these lenses had their own inherent drawbacks, including but not limited to lack of durability, imprecise optical characteristics, and in some cases difficult processability.

Recently, a number of compositions have been suggested and/or made which are useful in making hard or semi-hard contact lenses, which in turn offered some of the optical advantage of hard lenses, and which also offer greater gas permeability as a way of providing extended and more comfortable wear for the user. As with other commercial products, however, these products are capable of further improvement in one or more areas.

It is known that the cornea of the human eye requires a constant supply of oxygen. Consequently, hard contact lenses of increased gas permeability provide the potential for extended wear, and in some cases, improved user comfort in relation to prior hard lenses. An ideal contact lens permits the cornea of the eye to be comfortably bathed in lachrymal fluid, an to receive a continuing, fresh supply of atmospheric oxygen.

Such a lens should have a proper fit on the cornea so that it will remain in place without discomfort, preferably being able to be oriented so that it can provide proper astigmatic correction and, in many cases, offer the potential for a bifocal lens which may be precisely located on the eye and which will remain there in use.

An ideal lens is also one which will resist bacterial contamination and which may be cleaned from time to time by simple methods; in other words, one wherein elaborate procedures for sterilization are not required. Certain HEMA lenses suffered from the drawbacks of actual or potential ease of contamination and difficulty of cleansing.

Still further, an ideal lens is one which copes well with another conditions encountered in use, including resistance to collection of mucus, and retention of dimensional stability and optical characteristics in use on the eye. The patent literature contain numerous references to acrylic silanes per se, as well as reference to the combination of known polymerizable acrylic silane monomers with themselves or similar compounds, and with conventional polymerizable acrylate materials such as methyl acrylate, ethyl acrylate, and methyl methacrylate ("MMA"), for example. It is known to use conventional wetting agents such as N-vinyl pyrrolidone, methacrylic acid and the like, in conjunction with these materials and with cross-linking agents adapted to impart greater rigidity and other desirable characteristics to the finished product. These include ethyleneglycoldimethacrylate, triethyleneglycoldimethacrylate and other polyfunctional acrylates.

Typical patents referring to the general subject of these compositions include U.S. Pat. Nos. 3,377,371 (Quaal); 3,808,178 (Gaylord); and 4,216,303 (Novicky).

All of the foregoing patents describe compositions having certain gas permeability and other desirable characteristics. However, corneal contact lenses of the type referred to above are, and have been, capable of further improvement, including improvement in one or more desirable characteristics, and the ability to be manufactured from existing materials by known, repeatable methods.

The ability to make contact lenses having a relatively high permeability, and in particular, compatibility with other gas permeable polymers so that a fused type of bifocal lens can be made therefrom, are also desirable characteristics of improved contact lenses. In this connection, inasmuch as a fused bifocal contact lens normally includes a bifocal segment made from a different material than the distance vision segment, and by reason of having different front curvatures on two segments, it is inherently thicker than a normal single vision lens of the same power, and hence, less tolerant in use of materials having a low index of gas permeability.

According to the present invention, improved polymerizable silicates and polymers made from these silicates are able to be made which provide good chemical and physical characteristics, good optical characteristics, and other advantages, including high oxygen permeability in use.

It has been known that silicate materials have desirable characteristics, but certain prior art silicates have had drawbacks and disadvantages which have heretofore believed to prevent their effective use in applications such as copolymers in gas permeable contact lenses. According to the invention, compositions are provided which may be copolymerized with other acrylic materials, including other acrylic silicates, and organic acrylates of conventional types to make stable, gas permeable products.

In view of the failure of the prior art to provide reactive acrylic silicates and materials made therefrom which are suitable for use and manufacture of contact lenses, it is an object of the present invention to provide improved organic silicate materials.

Another object of the invention is to provide an acrylic silicate having siloxane portions and one or more sites rendering it reactive so as to be polymerizable and/or able to be cross-linked with methyl methacrylate, methacrylic acid, and acrylic acid and cross-linking agents such as polyfunctional acrylic esters.

Another object of the invention is to provide a composition which includes a siloxanyl or silyloxy acrylic silicate which is resistant to hydrolytic decomposition.

Still another object of the invention is to provide an improved acrylic siloxanyl silicate able to be copolymerized with known materials for the manufacture of gas permeable contact lenses.

A further object is to provide a method of making polymerizable acrylic silicate materials.

Another object of the invention is to provide a contact lens made from a material which includes siloxanyl acrylic silicate portion and acrylic portion, and having one or more cross-linking and wetting agents forming a part thereof.

A still further object of the invention is to provide a contact lens made from polymers which are in turn comprised in part from such silicate monomers.

Another object of the invention is to provide one or more acrylic silicate compositions wherein the acrylic portion is based on materials which make possible the production of a polymerizable silicate having methyl or ethyl acrylate comprising the acrylate portion as opposed to having the less reactive methyl methacrylate moiety forming such portions of the compositions.

Yet another object of the invention is to provide a reaction mechanism which permits the use of hydroxyethylmethacrylate (HEMA) or hydroxyethylacrylate (HEA) as a starting material rather than utilizing a methoxylated or ethoxylated methacryloxypropylsilane as a starting material in the production of a polymerizable monomer.

A further object of the invention is to provide one or more monomers wherein the polymerizable acrylic portion is based on HEMA or HEA, and wherein the silicon atom to which both the various siloxy or more complex groups of the acrylate portion are bonded to the acrylate containing portion by a carbon-oxygen-silicon linkage rather than the carbon silicon linkage characterizing prior art polymerizable acrylic silanes used for similar purposes.

Still another object is to provide a polymerizable silicate monomer having a terminal silicate group to which plural groups, such as sec-or-tert-butoxy groups, are used as substituents on silicon atoms which are bonded by an Si-O-Si linkage to the "terminal" silicon atom. The "terminal" atom as that term is used herein, means the silicon atom which forms a part of the C-O-Si linkage.

Another object is to provide a polymer of high oxygen permeability for non-optical uses, such as for use in analysis or treatment of blood or blood components, and for use in other medical or scientific apparatus.

The invention achieves these and other objects and advantages by providing acrylic silicates having the general formula:

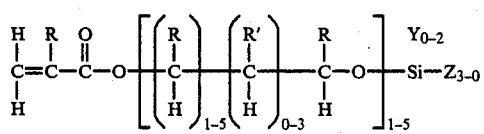

wherein
R = alkyl, aryl or H,
R' = R or OR
Y = alkyl, vinyl, aryl, or fluoroalkyl

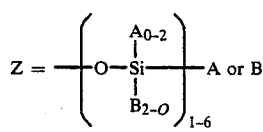

A = Y or H
B = oxyalkyl, oxyaryl, oxyfluoroalkyl, oxyalkylacrylate, alkyl esters, aryl esters, fluoroalkyl esters, or acrylic esters.

The invention also achieves its objects by providing specific reactive silicate materials and methods of making them, as well as polymerized acrylic materials made from these starting materials.

DESCRIPTION OF THE PREFERRED EMBODIMENTS OF THE INVENTION

By way of example, and not by way of limitation, the foregoing general formula points out that it is possible to provide a compound wherein one or more of the functional groups attached to the silicon atoms which in turn are attached to the primary functional or terminal silicon atoms may themselves be reactive or polymerizable acrylic esters. Consequently, it is possible to provide a produce which is capable of achieving cross-linking or further polymerization through these esters, rather than exclusively in polymerization achieved through polymerization of the "backbone" (of acrylic or methacrylic functional groups) in the composite molecule.

In the description herein, and in the claims, it is understood that the expression "alkyl" is intended to embrace cycloalkyl radicals as well as n-alkyl or iso-alkyl radicals, it being known, for example, that cyclohexylmethacrylate ("CHMA") is a compound desirable for inclusion in contact lenses. When used as a constituent of contact lens materials, CHMA provides excellent optical properties and hardness greater than that provided by polymers of methylmethacrylate alone.

While it will be understood that the invention may be practiced in different ways, and that the invention has utility other than that specifically described herein, such as utility in manufacturing things other than contact lenses, a description of the invention will be given by way of example wherein the product made is a corneal contact lens, wherein the composition includes an acrylic silicate ester made from an acrylic or lower alkyl acrylic ester silicate with the silicate portion having attached thereto a plurality of siloxane groups, preferably those substituted with highly branched alkyl groups such as sec-or tert-butoxysiloxanyl groups.

EXAMPLE 1

A composition for use in manufacturing a corneal contact lens was manufactured. The first step was the production of an acrylic silicate having trimethyl siloxy groups attached to a terminal silicon atom, which was in turn attached through the Si-O-C-linkage to an ethylmethacrylate radical, following which such acrylic silicate was reacted with one or more polymerizable acrylic esters, cross-linking agents, wetting agents and catalysts to produce a transparent rigid oxygen-permeable material from which a contact lens blank, and finally a contact lens, was made.

Part I.

A silicate ("C-I") having acrylate polymerizable acrylate functionality was prepared as follows:

To a 2 liter flask equipped with a stirrer was added 331 g. of Tris(trimethylsiloxy)chlorosilane, 90 g. of dry pyridine and 150 g. of hydroxyethyl methacrylate. The chlorosilane itself may be synthesized in a manner described in the literature, or may be purchased. After stirring the above mixture for one hour, the mixture was filtered and the product distilled under reduced pressure. A total of 425 ml of product (b.pt. 100° C.@1.0 mm Hg) was obtained. The product was indicated to be 99% pure by a gas-liquid chromatographic analysis. Infrared spectral analysis was consistent with the expected absorption bands for the proposed structure, as follows:

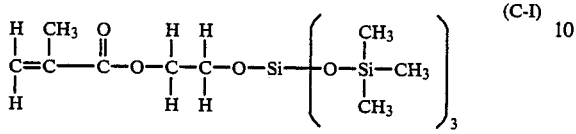

(C-I)

This compound may be referred to as tris(trimethylsiloxy)-2-methyacryloxy ethyl silicate.

Part II.

The above methacrylic silicate C-I was placed in a reaction mixture with additional ingredients as follows:

| Compound | Wt. Pct. |
| --- | --- |
| C-I | 30.0 |
| Methylmethacylate ("MMA") | 59.0 |
| Methacrylic acid ("MAA") | 6.0 |
| Cyclohexylmethacrylate ("CHMA") | 2.0 |
| Ethyleneglycoldimethacrylate ("EGDMA") | 3.0 |
| Catalyst(t-butylperoctoate) | 0.10 |
| Catalyst(t-butylperoxypivalate) (75%) | 0.05 |

The above ingredients were mixed and placed in a plurality of polyethylene tubes each containing about 50 ml liquid, and disposed in a vacuum oven previously purged with nitrogen so as to remove oxygen therefrom.

The oven was closed and the temperature held at 44° C. for 6 hours and then raised to 48°–50° C. for 18 additional hours.

The resulting product ("PM-1") is a clear, hard, transparent material which is resistant to hydrolytic decomposition.

The "PM-1" material is removed from the tubes, cut into a plurality of "buttons" or disks of about 0.5 to 1 cm in thickness and a diameter of about 1.5 cm. These buttons were then affixed to the headstock of a precision turning lathe, with test specimens and concavo-convex lenses being cut therefrom. Using a so-called Schema-Versatae Model 920 gas flux meter known and used in the contact lens industry, the DK of $10.0 \times 10^{-11}$ ml oxygen/cm$-^2$/155 mm Hg pressure was established at 37° C.

This material, in addition to being hydrolytically stable, displayed excellent physical properties; it was hard, rigid, transparent, and very importantly, was very machinable. I3 was able to be cut and polished into an extremely high quality corneal contact lens having a finished diameter of 7.5 mm and a thickness of 0.15 mm. The gas permeability of this material was good, but capable of further improvement. Accordingly, additional materials were made using more of the silicate material C-I in relation to the methyl methacrylate, for example.

EXAMPLE 2

It was desired to produce a contact lens material having increased oxygen permeability in relation to the lens shown in the foregoing example. Constituents were provided as follows:

| Compound | Wt. Pct. |
| --- | --- |
| C-I | 45.0 |
| (MMA) | 39.0 |
| (MAA) | 9.0 |
| (CHMA) | 3.0 |
| Triethyleneglycoldimethacrylate (TEGDMA) | 4.0 |
| Catalyst(t-butylperoctoate) | 0.10 |
| Catalyst(t-butylperoxypivalate) | 0.05 |

The ingredients listed above were mixed, cured, and analyzed in the same manner as their counterparts in Example 1, above. The resulting material ("PM-2") was hard, machineable, and transparent. The most significant difference between material "PM-1" and "PM-2" was that "PM-2", which contained 45% of the C-I material displayed an oxygen permeability, measured as outlined above, of 20.0 at 25° C., and 28.0 at 37° C. A highly desirable contact lens material was thus made utilizing this formula.

EXAMPLE 3

A material identical to that of Example 2 was made, except that, in place of methacrylic acid (MMA), N-vinyl 2-pyrrolidone was used as the wetting agent. This likewise produced a highly satisfactory product ("PM-3").

EXAMPLE 4

Another contact lens material was made using the manufacturing techniques and conditions described in connection with Examples 1–3 above, except that the following formula was used:

| Compound | Wt. Pct. |
| --- | --- |
| C-I | 55.0 |
| (MMA) | 28.0 |
| (MAA) | 9.0 |
| (CHMA) | 4.0 |
| (TEGDMA) | 4.0 |
| Catalyst (t-butylperoctoate) | 0.10 |
| Catalyst (t-butylperoxypivalate) | 0.05 |

This material, ("PM-4"), was similar to its counterparts described above, except that its oxygen permeability was measured at 30.0 at 25° C., and 41.0 at 37° C.

In some aspects of its physical properties, this material was not as desirable as the material from Examples 2 and 3, but it demonstrated the ability to be used as a contact lens material and showed a very high DK value, presently believed to be as high or higher than that obtainable with acrylic silane materials of a previously known kind.

EXAMPLE 5

Another contact lens material ("PM-5") was prepared using the conditions referred to above, except that the following proportions of ingredients were used:

| Compound | Wt. Pct. |
| --- | --- |
| C-I | 47.0 |
| (MMA) | 39.0 |
| (MAA) | 3.0 |
| (CHMA) | 10.0 |

| Compound | Wt. Pct. |
| --- | --- |
| (EGDME) | 1.0 |
| Catalyst | 0.2 |

The material just described, (PM-5) produced a very satisfactory contact lens having an excellent combination of oxygen permeability, optical clarity, machineability, hardness, and durability.

The DK for this material was tested and found to be 40.0 at 37° C.

The foregoing set of examples described the use of an acrylic silicate material described in Example 1, in making contact lenses using different proportions of other common known ingredients. From these examples, it may be generally asserted that there is a useful range of proportions in which these materials may be combined, with various "trade-offs" being made for whatever different combination of physical properties may be desired by the user. Using more of the acrylic silicate compound increases permeability up to and in some cases beyond 50, but certain properties may begin to deteriorate in respect to other desirable properties as the prortion of silicate material approaches and exceeds 50. Those skilled in the art realize that there is no one ideal material, and that the final product characteristics, costs, and other parameters may determine the exact makeup of the product actually used by the lens manufacturer.

Still further, it is known that there are additional uses of gas permeable acrylic materials, such as used in forming membranes or containers for blood, which may be purified by absorption of oxygen and/or increase or decrease in the concentration of other gaseous or vapor phase components. Other medical uses may be made of the novel materials described herein, including, but not limited to, use in the field of blood handling and treatment.

Referring again to the above formulations, it will be noted that the weight percentages aggregate 100% exclusive of the catalyst weight, it being understood that the catalysts are present in minor amounts relative to the other ingredients in the compositions, and that these calculations are made in this manner for simplicity.

EXAMPLE 6

Preparation of diethylene glycol α[tris(trimethylsiloxy)silyloxy]Ω-methacrylate.

The procedure of Example 1 is repeated except that instead of the HEMA of, Example 1 174 g of diethylene glycol monomethacrylate was added to a mixture containing 331 g of tris(trimethylsiloxy) chlorosilane and 90 g of pyridine. Purification by filtration and distillation as described provided about 300 g of the subject material having the formula:

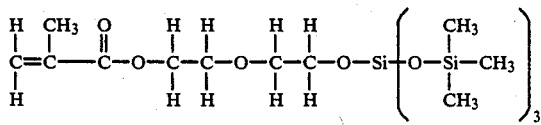

This compound may be referred to as diethylene glycol [tris(trimethylsiloxy)silyloxy]-methacrylate.

Using this material in place of the C-I monomer of Examples 1-5, and using the remaining ingredients referred to in such examples, hard, transparent, highly gas permeable plastic materials may be made.

This demonstrates the preparation of a gas permeable plastic optical material using a novel monomer characterized by a silicate portion, a polymerizable acrylic portion, and a diethyleneglycol type moiety joining these elements together in the monomer, which is then reacted with the remaining conventional ingredients of transparent acrylic-based plastic materials.

EXAMPLE 7

In carrying out this example, it was desired to produce a gas-permeable optical material using a novel acrylic silicate monomer, [tris(tri-sec-butoxysiloxy) silyloxy]ethyl-2-methacrylate. This was accomplished as follows:

A two liter flask equipped with a stirrer, thermometer and gas inlet tube below the liquid level was assembled in a dry ice alcohol cooling bath. To the flask was added 250 g of a mixture containing 50% Tris(tri-sec-butoxysiloxy) silane, one liter of hexane, and 40 g of pyridine. The mixture was cooled to −5° C. and chlorine gas was introduced under the liquid level until the mixture turned slightly yellow. The mixture was then purged with dry nitrogen at room temperature until the yellow color was removed. An additional 40 g of pyridine was added and 50 g of hydroxyethylmethacrylate (HEMA) was added dropwise. The mixture was then filtered and paramethoxyphenol was added as an inhibitor. Solvent and all low boiling components were removed by stripping the mixture under reduced pressure with a wipefilm evaporator. The product was further purified and decolorized by treatment with activated charcoal and alumina followed by several washings with 0.1 N sodium hydroxide, distilled water and drying with anhydrous sodium sulfate. The resulting structure may be represented as follows:

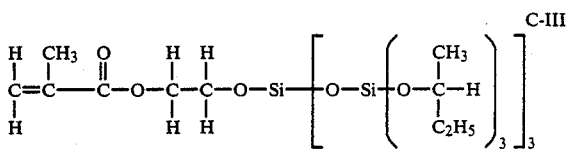

This compound may be referred to as [tris(tri-sec-butoxysiloxy)]silyloxy ethyl-2-methacrylate.

Preparation of an optical material (PM-6) was then carried out using monomer C-III referred to just above. The optical material was used by performing the process referred to in Example 2, except that 45.0% by weight of compound C-III was used in place of the same amount of compound C-I. The resulting compound is suitable for use as a contact lens material, having a suitable oxygen permeability or "DK".

As pointed out in the foregoing objects and elsewhere herein, increased oxygen permeability in the final plastic product is achieved by the use of composite polymers having polymerizable ester groups, such as acrylates or substituted acrylates, forming one portion of the monomer, suitable silicates forming another part of the monomer, and coupling moieties formed from reactive alcohol groups (such as the hydroxyl groups in HEMA) forming the remainder of the molecule. As noted from the above examples, the invention provides a number of additional polymerizable acrylic silicates of various types. These compositions are all polymerizable acrylic silicates even though they may differ, among themselves, as to (a) the acrylate group per se (b) the linking or hydroxyl-based group per se, and (c) the group attached to the terminal or silicate atom per se.

Compounds specifically referred to herein differ from prior art materials, for example, in providing acrylic silicates rather than acrylic silanes. These are illustrated by the following compounds C-IV to C-XVII, inclusive, such compounds being set forth as Examples 9-20, inclusive.

EXAMPLES 9-20

The novel silicate set forth below is useful in practice in the invention:

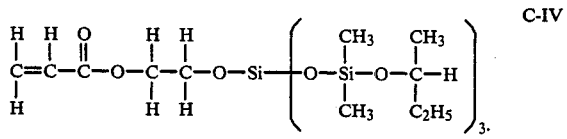

Using the above classification of moieties, (the "a" group being an acrylate group, the "b" group being a diol linking group and the "c" group being a siloxane group, the acrylate group in C-IV is an acrylate group per se rather than a methacrylate group; the linking group is based on ethyleneglycol, and the siloxane groups are three (sec-butoxy dimethyl siloxy) groups.

A composition identified as Compound C-V is illustrated below:

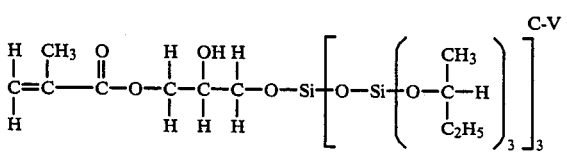

According to the above scheme, the basic acrylate group is a methacrylate group, the linking alcohol group is glycerol, and the silicate group is similar to that in Compound C-IV, except that it includes the Tris-(tri-sec-butoxysiloxy) silyloxy group.

Compound VI also is useful in practicing the invention. Its structure is as follows:

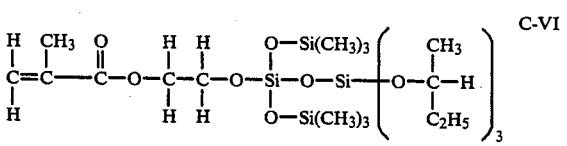

In this composition, a methacrylic group is present; the alcohol group is based on ethyleneglycol, and the terminal silicate atom has bonded thereto two trimethylsiloxy groups as well as one tris-(sec-butoxy)siloxy group.

The invention may be practiced using a compound such as C-VII, illustrated as follows:

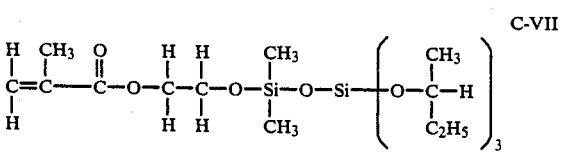

This compound is one wherein the acrylate group is a methacrylate group, the linking alcohol portion is based on ethylene glycol, and the "C" group includes three tris(sec-butoxy)siloxy groups as well substituted therein.

Another composition suitable for practicing the invention may be made using the monomer illustrated as C-VIII:

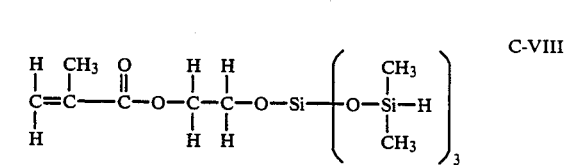

This compound is a methacrylate which includes a ethyleneglycol based linking group and wherein the silicate group is relatively simple in that its substituents include three dimethylsiloxane groups.

Another compound, C-IX, is also useful in practicing the invention. This compound has the structure illustrated below:

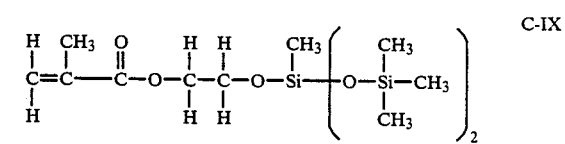

This composition is similar to that of C-VII insofar as it is based on an HEMA; however, the silicon atom bonded to the glycol linkage includes two trimethylsiloxy substituents and one methyl substituent.

Another composition suitable for use in the invention is illustrated as compound C-X. This structure is illustrated as follows:

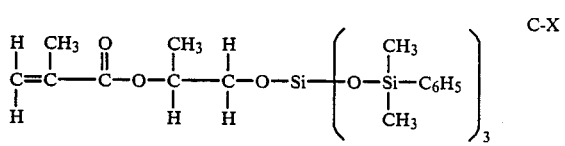

This composition is a methacrylate composition using a propylene oxide-based linking group. The silicate atom, in this case, however, is substituted with three dimethylphenylsiloxy groups.

Another compound useful in practicing the invention is a compound C-XI having the following structure:

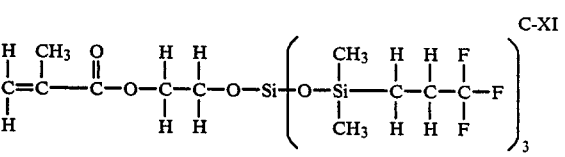

This compound is based on HEMA, and illustrates the use of fluoro substituted alkanes as substituents on the siloxy group attached to the silicate portion of the molecule.

Another fluorine containing composition is useful in practicing the invention. This compound, whose structure is illustrated below, is identified as C-XII.

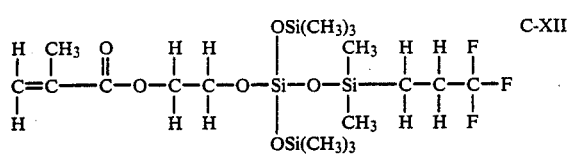

C-XII

This composition resembles that of C-XI, except that the groups substituted on the terminal silicate atom include two trimethylsiloxy groups and a single 3,3,3-trifluoropropyldimethylsiloxane group.

A composition such as C-XIII also falls within the scope of the invention. This compound is illustrated below:

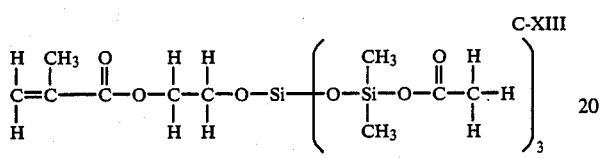

C-XIII

As noted from the above structure, this compound is a hydroxyethylacrylate-based silicate which includes as the substituent on the terminal silicate atom three dimethylacetoxysiloxy substituents.

The foregoing example C-XIII illustrates an ester substitution in the siloxane attached to the silicate atom.

Another composition falling within the ambit of the present invention is illustrated below.

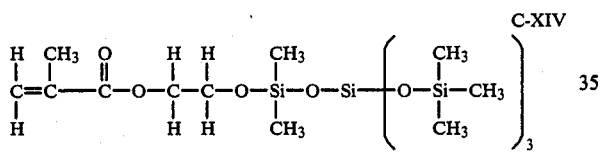

C-XIV

As illustrated above, this compound is based on HEMA, and contains a dimethylsiloxane group to which a tris(trimethylsiloxy) silyloxy group has been added.

A still further composition which embodies the present invention is illustrated as compound C-XV which structure is shown below:

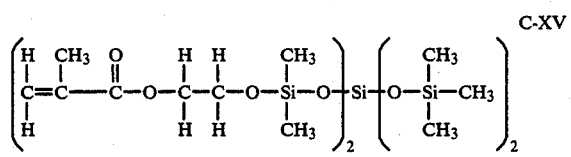

C-XV

This composition contains difunctional methacrylate functionality, and of course, could include difunctional unsubstituted or further substituted acrylate functionality. The illustrated composition includes two trimethylsiloxy substituents as well as two dimethylsiloxane groups, one being attache dot each of the polymerizable acrylic groups.

Referring now to the two immediately preceeding Examples, composition C-XIV and C-XV, rather than being prepared as referred to above, are prepared by another method fully within the scope of the invention and described below:

To a five liter flask equipped with a stirrer, additional funnel and a thermometer, and assembled in a cold water cooling bath, are added two moles of ethyl ortho silicate (418 g), 6 moles of trimethylacetoxy silane (792 g) and two moles of dimethylacetoxysilane (240 g). To this mixture is added dropwise 75 g of a mixture of equal parts by weight of sulfuric acid, ethanol and water. The temperature rises to about 40° C. The mixture is then washed three times with water, and the ethyl acetate thus formed is removed by distillation under reduced pressure. The resulting mixture, as determined by gas chromatography analysis, included five structures present in the amounts indicated below:

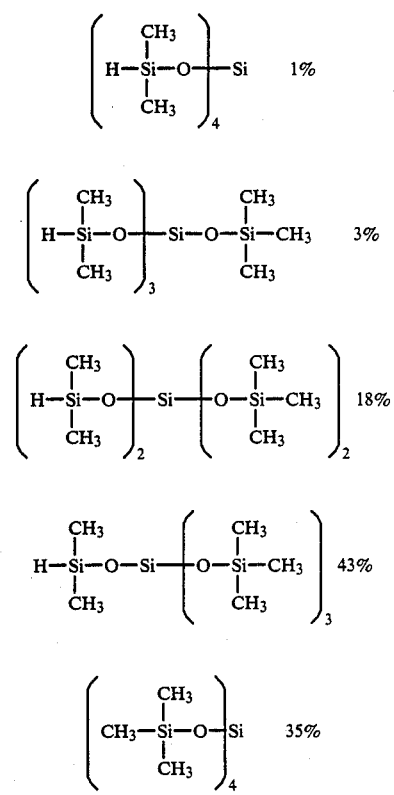

To this mixture is added an equal amount of n-hexane. A cooling bath capable of holding the reaction temperature at 0° C. is used. Chlorine gas is then added to the mixture. The hydrogen chloride formed may be exhausted into a flask containing water and sodium bicarbonate. When the mixture becomes yellow, the excess chlorine and most of the hydrogen chloride are removed by purging the gas inlet tube with dry nitrogen.

To this mixture is further added sufficient pyridine to neutralize the remaining hydrogen chloride and to equal the moles of hydroxy ethyl methacrylate (HEMA) next added to the mixture. HEMA is then added until no more precipitation of pyridine hydrochloride is noted. The mixture is then filtered and distilled under reduced pressure to isolate the mono- and di-adduct derivatives of the HEMA addition having the structures shown a C-XIV and C-XV.

Two additional examples of materials fully within the scope of the invention are slight variations of the above specific examples. These are:

EXAMPLE 21

$$\underset{H}{\overset{H}{|}}C=\underset{H}{\overset{CH_3}{|}}C-\overset{O}{\overset{\|}{C}}-O-\underset{H}{\overset{CH_3}{|}}C-\underset{H}{\overset{H}{|}}C-O-Si\left(-O-\underset{CH_3}{\overset{CH_3}{|}}Si-CH_3\right)_3 \quad (XVI)$$

EXAMPLE 22

$$\left(\underset{H}{\overset{H}{|}}C=\underset{}{\overset{CH_3}{|}}C-\overset{O}{\overset{\|}{C}}-O-\underset{H}{\overset{H}{|}}C-\underset{H}{\overset{H}{|}}C-O\right)_2 Si\left(-O-\underset{CH_3}{\overset{CH_3}{|}}Si-CH_3\right)_2 \quad (XVII)$$

Inasmuch as stable silicates or alkoxy silanes can be made by the use of higher molecular weight or sterically hindered alcohols, it is possible, according to the invention, and in some cases preferred, to prepare such stable organo-functional silicates or alkoxy silanes by the use of hydroxy-functional acrylate or substituted acrylate esters. Such esters are commonly prepared by the addition of epoxy functional hydrocarbons such as, but not limited to, ethylene oxide, propylene oxide, 2-butylenoxide, cyclohexeneoxide, etc., to acrylic or substituted acrylic acids. Such esters may also be made by the preparation of so-called half esters resulting from the addition of diols or polyols, such as, but not limited to, ethylene glycol, so-called diethylene glycol, propylene glycol, glycerol, certain celluloses, etc., to acrylic or substituted acrylic acids. Preparation of these compounds may be accomplished by ester exchange of low molecular weight acrylate or substituted acrylates with the appropriate diol or polyol.

Such preparations may also be made by the reaction of acrylic or substituted acrylic anhydrides with the appropriate epoxy or polyol compound.

It will thus be seen that the present invention provides novel acrylic silicate compositions, methods of making them, and prfoucts made therefrom, such compositions, methods, and products having a number of advantages and characteristics, including those pointed out herein, and others which are inherent in the invention.

Various examples of the practice of the invention having been set forth by way of example, it is anticipated that variations and modifications to the examples set forth herein will occur to those skilled in the art, and that such changes and modifications may be made without departing from the scope of the invention or the spirit of the appended claims.

I claim:

1. An oxygen permeable plastic material comprising the reaction product of from about 10% to about 90% by weight of a polymerizable acrylic or methacrylic ester, and substituted or unsubstituted acrylic silicate from about 10% to about 90% by weight of a polymerizable silicate having the structure:

$$\underset{H}{\overset{H}{|}}C=\underset{}{\overset{R}{|}}C-\overset{O}{\overset{\|}{C}}-O-\left[\left(\underset{H}{\overset{R}{|}}C\right)_{1-5}\left(\underset{H}{\overset{R'}{|}}C\right)_{0-3}\underset{H}{\overset{R}{|}}C-O\right]_{1-5}\underset{}{\overset{Y_{0-2}}{|}}Si-Z_{3-0}$$

wherein
R = alkyl, aryl or H,
R' = R or OR
Y = alkyl, vinyl, aryl, or fluoroalkyl $$Z = \left(-O-\underset{B_{2-O}}{\overset{A_{0-2}}{|}}Si-\right)_{1-6} A \text{ or } B$$

A = Y or H and
B = oxyalkyl, oxyaryl, oxyfluoroalkyl, oxyalkylacrylate, alkyl esters, aryl esters, fluoroalkyl esters, or acrylic esters.

2. As a new article of manufacture, a contact lens of improved oxygen permeability, said lens being made from a transparent plastic material which comprises the reaction product of from about 10% to about 90% by weight of a polymerizable acrylic or methacrylic ester, and substituted or unsubstituted from about 10% to about 90% by weight of a polymerizable silicate having the structure:

$$\underset{H}{\overset{H}{|}}C=\underset{}{\overset{R}{|}}C-\overset{O}{\overset{\|}{C}}-O-\left[\left(\underset{H}{\overset{R}{|}}C\right)_{1-5}\left(\underset{H}{\overset{R'}{|}}C\right)_{0-3}\underset{H}{\overset{R}{|}}C-O\right]_{1-5}\underset{}{\overset{Y_{0-2}}{|}}Si-Z_{3-0}$$

wherein
R = alkyl, aryl or H,
R' = R or OR
Y = alkyl, vinyl, aryl, or fluoroalkyl $$Z = \left(-O-\underset{B_{2-O}}{\overset{A_{0-2}}{|}}Si-\right)_{1-6} A \text{ or } B$$

A = Y or H and
B = oxyalkyl, oxyaryl, oxyfluoroalkyl, oxyalkylacrylate, alkyl esters, aryl esters, fluoroalkyl esters, or acrylic esters, and the remainder comprising from about 0% to about 20% by weight of a mixture of compatible wetting agents, cross-linking agents, and catalysts.

3. A contact lens as defined in claim 2 wherein said cross-linking agents include
ethyleneglycoldimethacrylate
diethyleneglycoldimethacrylate
triethylene glycoldimethacrylate
tetraethyleneglycoldimethacrylate
polyethyleneglycoldimethacrylate,
and a composition having the structure:

$$\left(\underset{H}{\overset{H}{|}}C=\underset{}{\overset{CH_3}{|}}C-\overset{O}{\overset{\|}{C}}-O-\underset{H}{\overset{H}{|}}C-\underset{H}{\overset{H}{|}}C-O-\underset{CH_3}{\overset{CH_3}{|}}Si-O\right)_2 Si\left(-O-\underset{CH_3}{\overset{CH_3}{|}}Si-CH_3\right)_2.$$

4. A contact lens as defined in claim 2 wherein said wetting agent is selected from the glass consisting of methacrylic acid and N-vinyl 2-pyrrolidone.

* * * * *